United States Patent [19]
Shei et al.

[11] Patent Number: 5,569,238
[45] Date of Patent: Oct. 29, 1996

[54] ENERGY DELIVERY SYSTEM CONTROLLABLE TO CONTINUOUSLY DELIVER LASER ENERGY IN PERFORMING PHOTOREFRACTIVE KERATECTOMY

[76] Inventors: Sun-Sheng Shei; Ta-Ming Fang, both of Massachusetts Technological Laboratory, 330 Pleasant St., Belmont, Mass. 02178

[21] Appl. No.: 326,658

[22] Filed: Oct. 19, 1994

[51] Int. Cl.⁶ ................................................ A61N 5/06
[52] U.S. Cl. ................................ 606/4; 606/5; 606/17
[58] Field of Search ................................ 606/4, 5, 6, 10, 606/11, 12, 17

[56] References Cited

U.S. PATENT DOCUMENTS

| | | | |
|---|---|---|---|
| 4,718,418 | 1/1988 | L'Esperance, Jr. | 606/4 |
| 4,729,372 | 3/1988 | L'Esperance, Jr. | 606/4 |
| 4,911,711 | 3/1990 | Telfair et al. | 606/5 |
| 5,376,086 | 12/1994 | Khoobehi et al. | 606/4 |
| 5,411,501 | 5/1995 | Klopotek | 606/5 |
| 5,461,212 | 10/1995 | Seiler et al. | 606/5 |
| 5,470,329 | 11/1995 | Sumiya | 606/5 |
| 5,505,723 | 4/1996 | Muller | 606/5 |

*Primary Examiner*—Angela D. Sykes
*Assistant Examiner*—Sonya Harris-Ogugua

[57] ABSTRACT

The present invention discloses an optical system for performing a laser photorefractive keratectomy operation on a cornea for vision correction. The optical system comprises a laser source emitting a laser beam. The optical system also includes a beam processing subsystem for receiving and processing the laser beam for generating a processed laser beam suitable for performing the keratectomy operation. The optical system further includes an energy delivery subsystem including a continuous energy-delivery control device which may include time-varying movable slits, rotating diaphragms, or combination of lens system with moving screen, for optically controlling the energy delivered to different areas of the cornea by the processed laser beam for performing the vision correction.

11 Claims, 9 Drawing Sheets

Our Laser Energy Delivery System

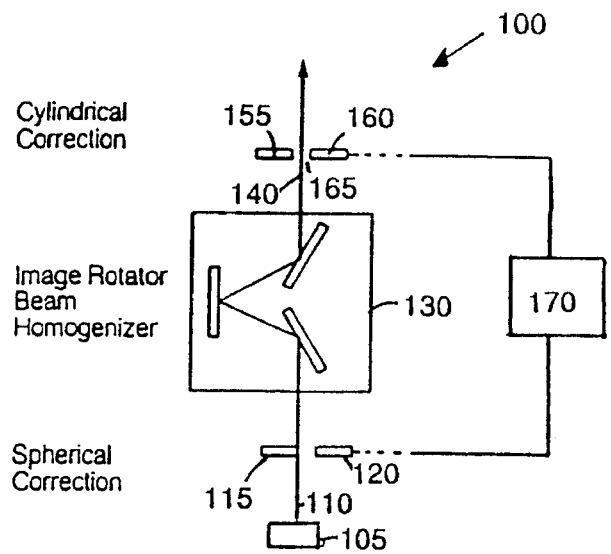
Figure 2. Our Laser Energy Delivery System
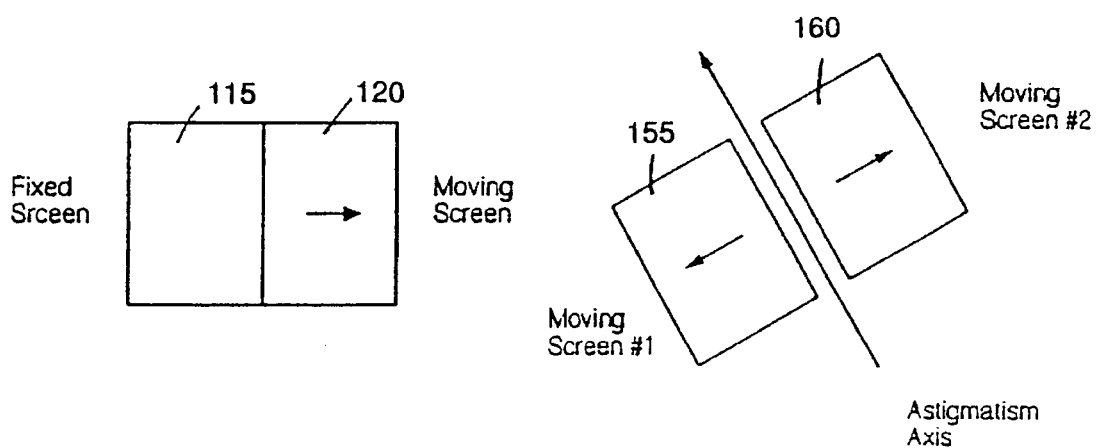
Figure 3. Moving Slit Shutter System for Myopia and Hyperopia Correction
Figure 4. Moving Slit Shutter System for Astigmatism Correction

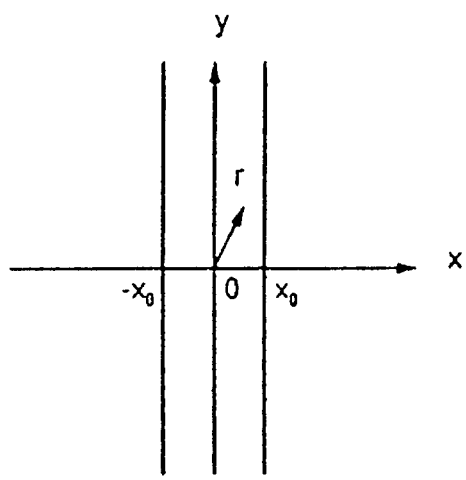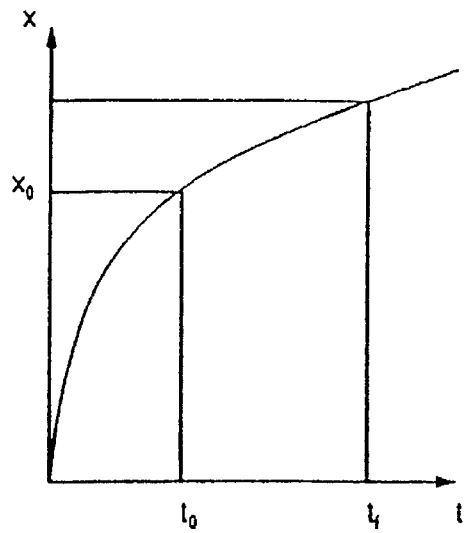
Figure 5. Diagram Describing Motion of Slits for Cylindrical Correction
Figure 6. The Function of x in time t
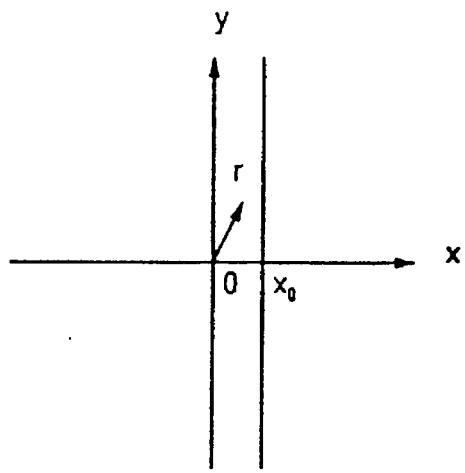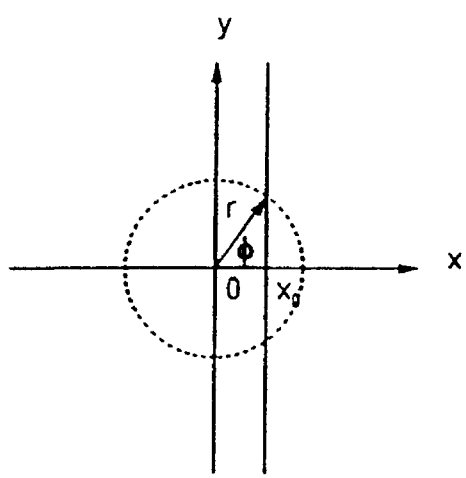
Figure 7. Diagram Describing Motion of Slit for Myopia Correction
Figure 8. Diagram Describing Equation 7

ENERGY DELIVERY SYSTEM CONTROLLABLE TO CONTINUOUSLY DELIVER LASER ENERGY IN PERFORMING PHOTOREFRACTIVE KERATECTOMY

BACKGROUND OF THE INVENTION

1. Field of the Invention

This invention relates generally to the design of energy delivery system in laser photorefractive keratectomy. More particularly, this invention relates to the design of the energy delivery system in laser photorefractive keratectomy which utilizes continuous energy-delivery control means such as time-varying moving shutters or rotating diaphragms, or lens system, which may be controlled by a computer to continuously deliver the laser energy onto the surface of a cornea for correction of myopia, hyperopia, or astigmatism.

2. Description of the Prior Art

Conventional laser photorefractive keratectomy is limited by several technical difficulties due to the use of discrete aperture masks. On the one hand, the efficiency of conventional photorefractive keratectomy in applying laser beam to the cornea for correction of myopia, hyperopia, and astigmatism is limited by the number of discrete aperture masks on the aperture wheels and the time required for changing aperture masks and realigning the optical system. On the other hand, the result of the laser operation with the use of discrete masks will lead to ablation of cornea tissues in the form of discrete stepped rings. In order to achieve smoother laser ablation of the cornea, it is desirable to increase the number of masks in the aperture wheel. However, this would require more time consuming processes in changing the aperture masks and optical realignment thus make the entire process even slower and more expensive.

The diagram in FIG. 1A shows the optical design of a typical laser photorefractive keratectomy (PK) system 10. An excimer laser source 15 is used for applying the energy for removing different amount of cornea tissues depending on the corrections required for that specific operation. The extremely short pulse duration of the excimer laser (ten to twenty nanoseconds) would decrease the undesirable thermal effects on the cornea surface to a theoretically infinitesimal level because of the apparent lack of time for thermal diffusion. The output beam 20 from the excimer laser 15 may have irregularities including high energy spots, i.e., hot spots, which need to be processed before the laser beam can be applied to the cornea. A beam processing system 25 is used to smooth out and reshape the laser beam profile. The beam processing system 25 may include optical components such as shutters, mirrors, beam scrapers, anamorphic prisms, etc. After passes through the beam processing system 25, the laser beam 20 is transmitted to an image rotator-beam homogenizer 30 which homogenizes and converts the laser beam into a circular beam.

The photorefractive keratectomy (PK) system 10 also includes a myopia wheel 35, an astigmatisms wheel 40, a hyperopia wheel 45 and beam directing system 50 for directing the laser beam to the surface of a cornea 60 to be operated. The beam directing system may includes various optical components such as mirrors, safety shutters, zoom lenses, beam splitter, etc. to accurately direct the beam to the cornea 60. FIGS. 1B, and 1C show the myopia aperture wheel 35 and the hyperopia aperture wheel 45 respectively wherein the oversize apertures are shown for the purpose of illustration. The myopia aperture wheel 35 employs various decreasing-diameter apertures while the hyperopia aperture wheel 45 employs annular apertures of decreasing radial width. For the purpose of vision correction, the mechanism applied by the PK system 10 is to allow each position of the wheel to remain an appropriate number of pulses such that precise amount of ablazing energy may be delivered to the cornea 60 for removing a piece of cornea tissue for correcting the vision.

FIGS. 1D and 1E show the myopia correction profile and hyperopia correction profile respectively wherein the initial surface, the desired surface and the actual ablated surface resulting from the correction operation are shown. For myopia correction, more of the central tissue from the cornea 60 is removed in order to flatten the cornea curvature by a series of stepwise enlargements of the beam impacting on the cornea. The length of time that the aperture opening remains at each of these stations on the myopia wheel 35 is precisely calculated and controlled by a computer (not shown). In FIG. 1E, the operation employs aperture masks of progressive enlarging annuli such that greater amount of peripheral corneal tissues are removed in order to steepen the curvature of the cornea surface to correct the hyperopia refractive condition.

The stepwise profiles as that shown in FIGS. 1D and 1E clearly illustrate the undesirable effects caused by the use of these discrete aperture masks. Additionally, the efficiency of the operation is adversely affected by the time and processes required to change the aperture masks and the realignment of the optical system every time when a new mask is used. Since an optical system as that shown in FIG. 1A with the discrete aperture masks mounted on the aperture wheels, e.g., aperture wheels 35, 40 and 45, are commonly employed by the conventional PK systems marketed by Taunton Technologies, VISX, or Meditec, further improvements of the energy delivery system are till required to overcome this technical limitation.

Therefore, a need still exits in the art of laser energy delivery system in photorefractive keratectomy for a new technique to resolve the technical difficulties discussed above. Specifically, the energy delivery system must be able to eliminate the use of the discrete aperture masks in order to achieve smooth laser ablation on the cornea. Meanwhile, the new PK energy delivery system must be controlled with high degree of precision while shortening the surgery time and furthermore providing more operational flexibility thus capable of accommodating different excimer laser beam profiles.

SUMMARY OF THE PRESENT INVENTION

It is therefore an object of the present invention to provide a new technique in the design of the energy delivery system for photorefractive keratectomy to overcome the aforementioned difficulties encountered in the prior art.

Specifically, it is an object of the present invention to provide an energy delivery system for photorefractive keratectomy to produce smooth laser ablation on the cornea for vision correction by utilizing moving screens under computer control to deliver precise laser energy to the cornea.

Another object of the present invention is to provide an energy delivery system for photorefractive keratectomy such that the efficiency of operation can be improved without requiring the change of aperture masks and realignment of the optical system.

Another object of the present invention is to provide an energy delivery system for photorefractive keratectomy such that the surgery time can be shortened by eliminating the requirement of changing the aperture masks and the realignment of the optical system.

Another object of the present invention is to provide an energy delivery system for photorefractive keratectomy such that the moving screen is now utilized under the control of computer such that higher precision of vision correction can be achieved while human errors in operation can be reduced.

Briefly, in a preferred embodiment, the present invention discloses an optical system for performing a laser photorefractive keratectomy operation on a cornea for vision correction. The optical system comprises a laser source emitting a laser beam. The optical system also includes a beam processing means for receiving and processing the laser beam for generating a processed laser beam suitable for performing the keratectomy operation. The optical system further includes an energy delivery means including a continuous energy-delivery control means which may include control means such as include time-varying movable means, rotating diaphragms, or combination of lens system with moving screen, for optically controlling the energy delivered to different areas of the cornea by the processed laser beam for performing the vision correction. In another preferred embodiment, the energy delivery means including the time-varying movable means are being controlled by a microprocessor. In yet another preferred embodiment, the time-varying movable means includes at least one moving optical shutter.

It is an advantage of the present invention that it provides an energy delivery system for photorefractive keratectomy to produce smooth laser ablation on the cornea for vision correction by utilizing moving screens under computer control to deliver precise laser energy to the cornea.

Another advantage of the present invention is that it provides an energy delivery system for photorefractive keratectomy such that the efficiency of operation can be improved without requiring the change of aperture masks and realignment of the optical system.

Another advantage of the present invention is that it provides an energy delivery system for photorefractive keratectomy such that the surgery time can be shortened by eliminating the requirement of changing the aperture masks and the realignment of the optical system.

Another advantage of the present invention is that it provides an energy delivery system for photorefractive keratectomy such that the moving screen is now utilized under the control of computer such that higher precision of vision correction can be achieved while human errors in operation can be reduced.

These and other objects and advantages of the present invention will no doubt become obvious to those of ordinary skill in the art after having read the following detailed description of the preferred embodiment which is illustrated in the various drawing figures.

BRIEF DESCRIPTION OF THE DRAWINGS

FIG. 2 is a system functional diagram of a laser energy delivery system of the present invention;

FIG. 3 shows a moving screen shutter used for myopia and hyperopia corrections in the laser energy delivery system of the present invention;

FIG. 4 shows a moving screen shutter used for the astigmatism corrections in the laser energy delivery system of the present invention;

FIG. 5 is a diagram describing the motion of slits for cylindrical correction;

FIG. 6 shows the function of distance of movement, i.e., x, in relationship to time t of the slits of FIG. 5;

FIG. 7 is a diagram describing the motion of slit for myopia correction;

FIG. 8 shows the functional relationship according to Equation 9;

DETAILED DESCRIPTION OF THE PREFERRED EMBODIMENT

Figure 1A:
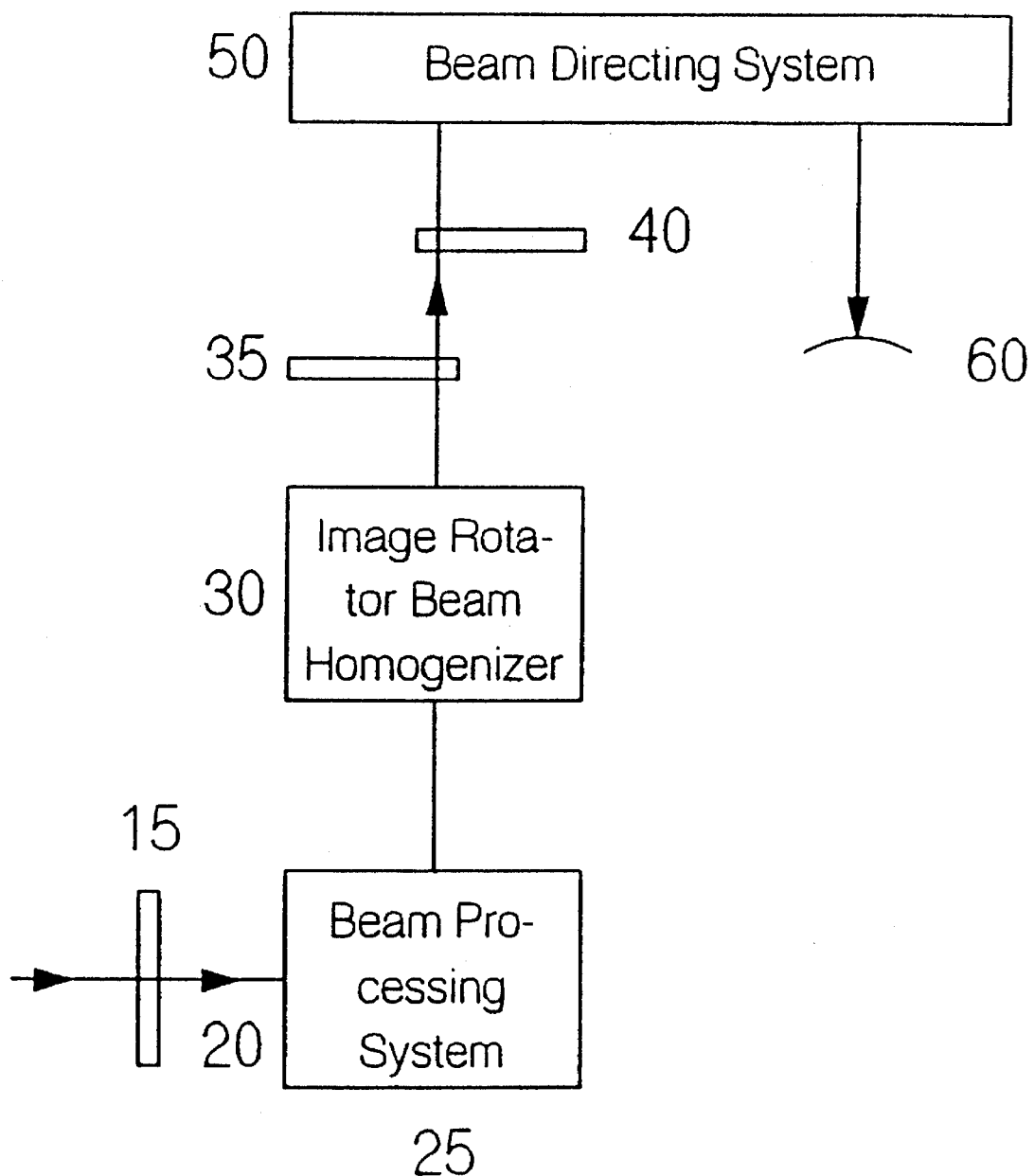
FIG. 1A is a system functional diagram of a laser energy delivery system of a prior art design.
Figure 1B:
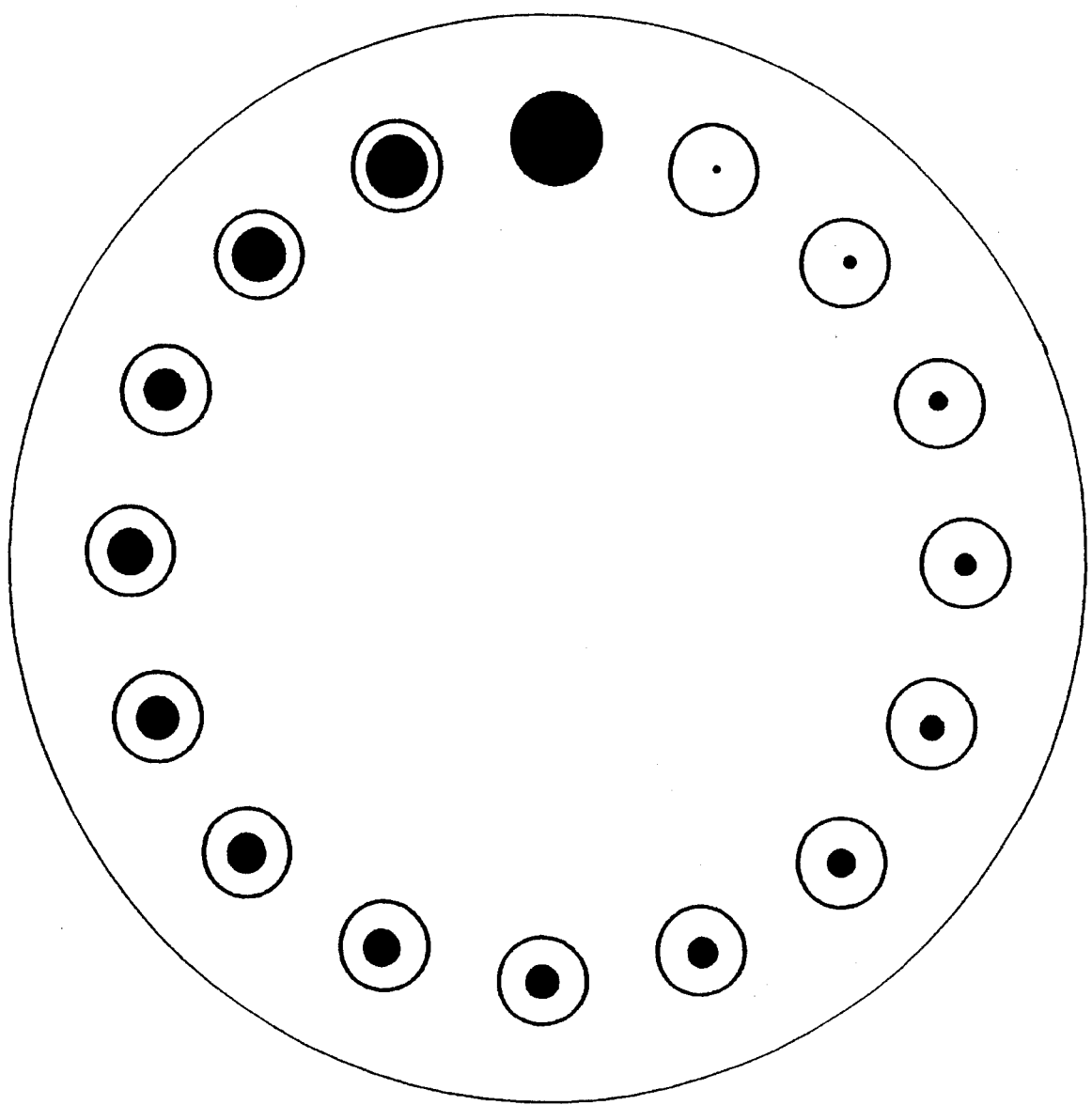
FIG. 1B is a diagram showing a myopia aperture wheel employed in the laser energy delivery system of FIG. 1A.
Figure 1C:
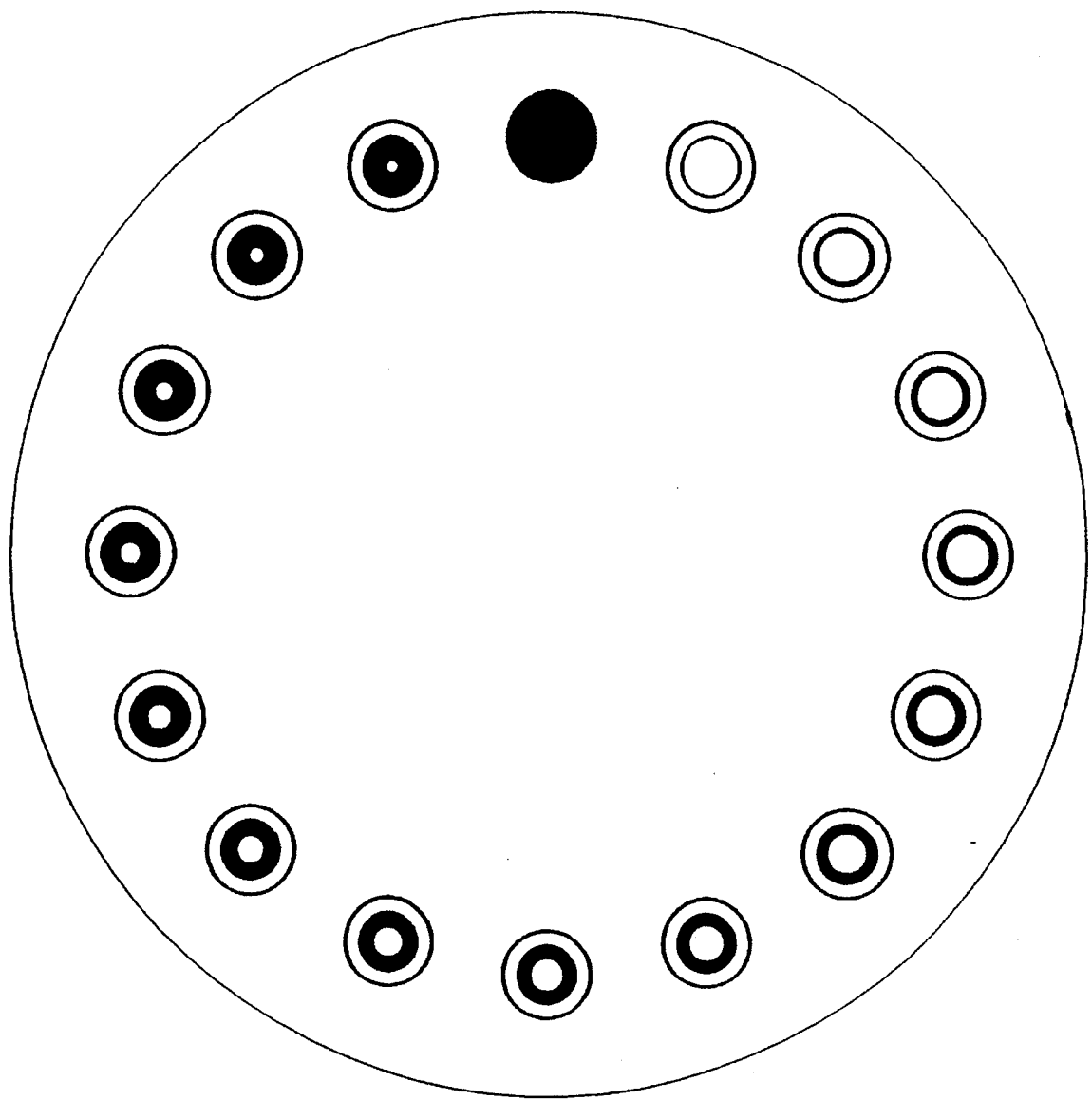
FIG. 1C is a diagram showing a hyperopia aperture wheel employed in the laser energy delivery system of FIG. 1A.
Figure 1D:
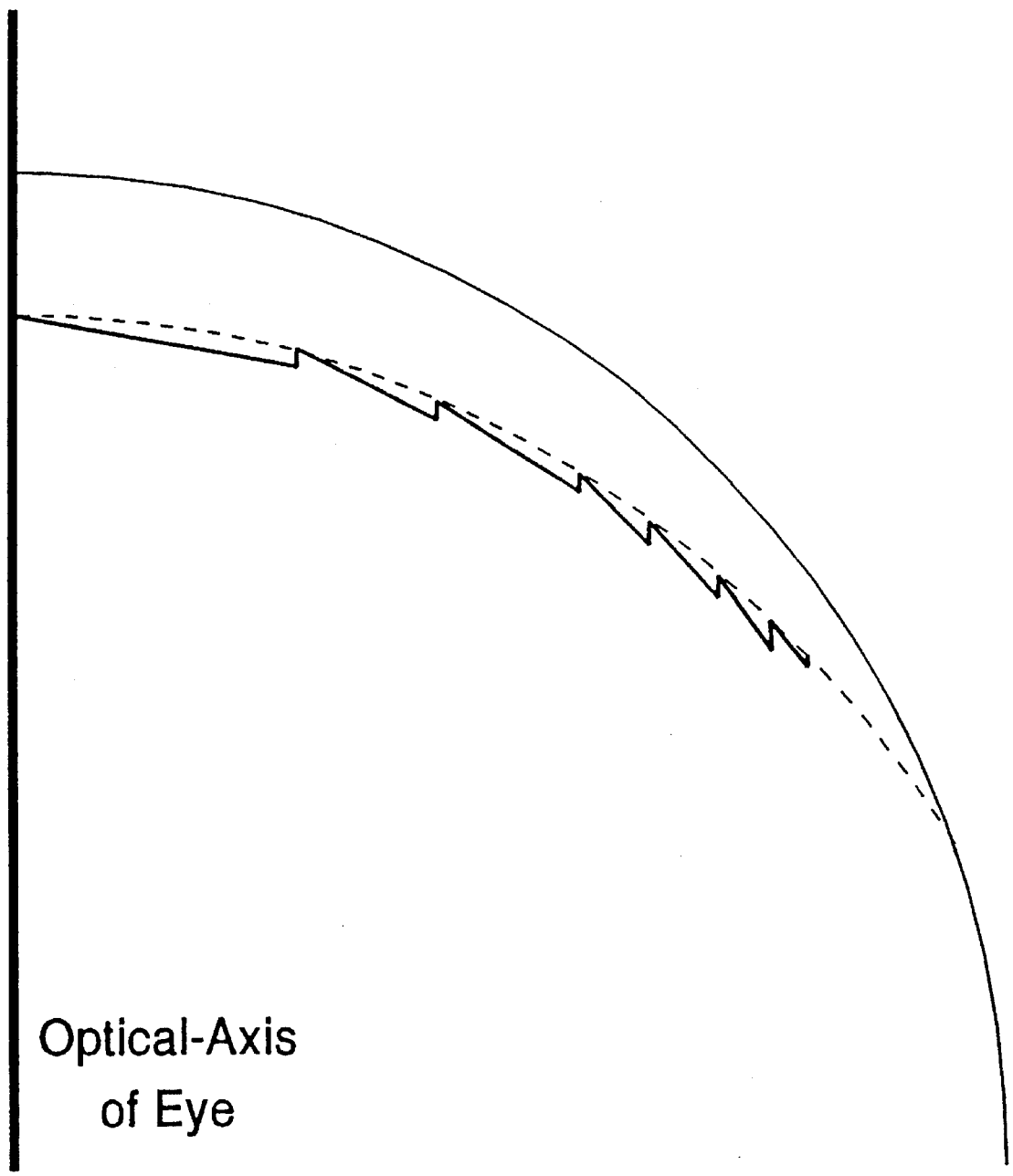
FIG. 1D shows a myopia correction profile utilizing the myopia aperture wheel of FIG. 1B.
Figure 1E:
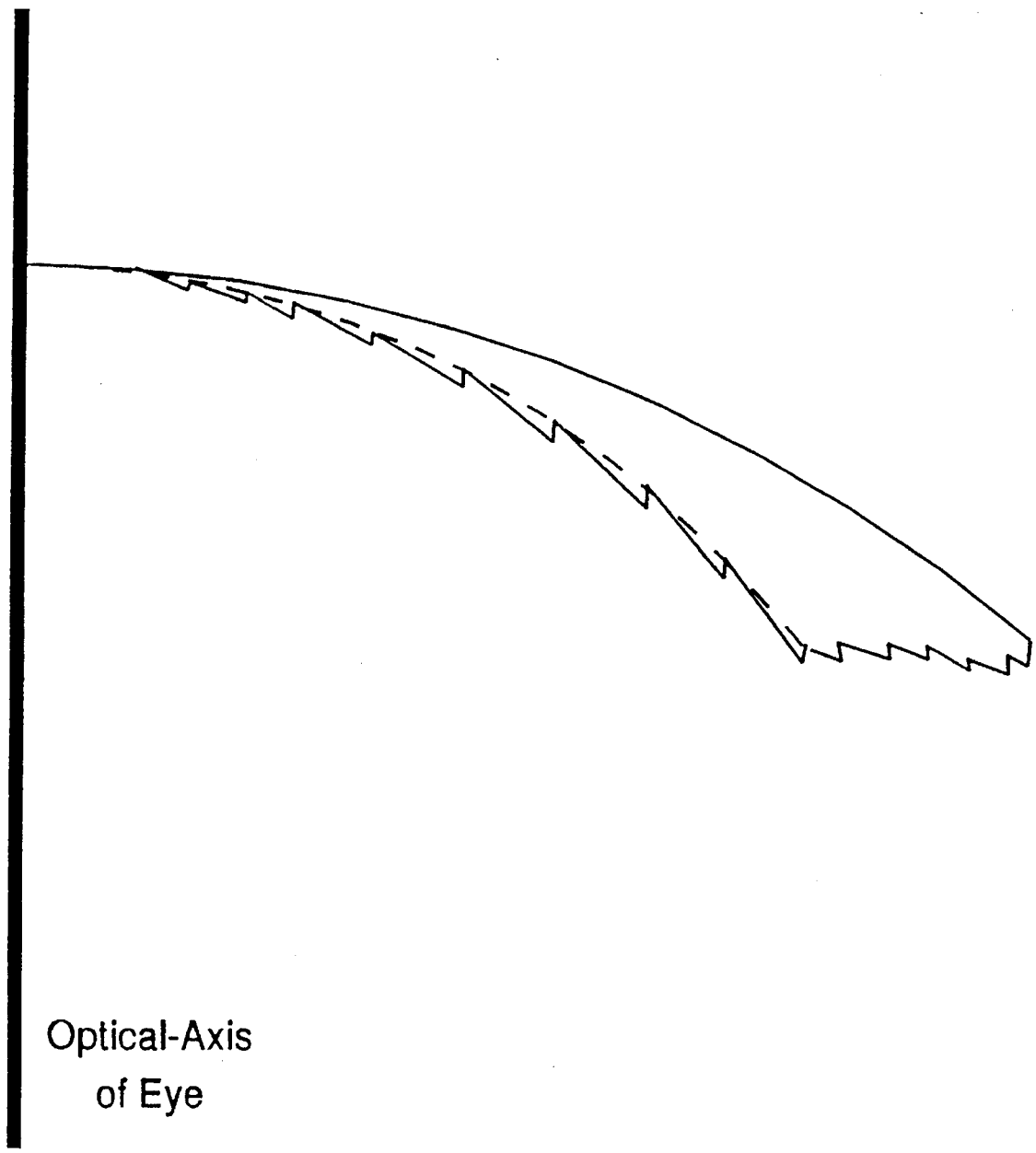
FIG. 1E shows a hyperopia correction profile utilizing the hyperopia aperture wheel of FIG. 1C.

FIG. 2 is a functional diagram showing the optical path and system configuration of a laser energy delivery system 100 for performing the photorefractive keratectomy according to the design of the present invention. A laser source 105 emitting a beam 110 is first received and processed by a spherical correction means, i.e., a myopia/hyperopia correction means, of a continuous energy delivery control means which is a moving slit shutter in this preferred embodiment including two opaque screens 115 and 120 wherein the first screen 115 is fixed and the second screen 120 is a moving screen. Before the screen 120 moves to the right, it is in contact with the fixed screen 115 thus blocking the laser beam 110 from passing through. As shown in FIG. 3, as the screen 120 is caused to move to the right in a continuous manner, an slit of increasing width is opened allowing increasing amount of laser energy to pass through. By employing this continuous energy delivery control means including two opaque screens, the moving screen 120 is also controllable to move from an originally open position to the left thus gradually decreasing the width of the slit and the laser energy pass through.

After passing through the slit between the screens 115 and 120, the laser beam 110 arrives at an image rotator and beam homogenizer 130 which processes and reshapes the laser beam 110 into a circular beam which is symmetric with respect to the optical axis of the laser beam 110. The circular beam 140 generated by the image rotator and beam homogenizer 130 are received and processed by a astigmatism correction means 150 of the continuous energy delivery control means. In this preferred embodiment, the astigmatism correction means 150, which is a cylindrical correction means as shown in FIG. 2, also includes two opaque screens 155 and 160 wherein the opening slit 165 is aligned with the axis of the astigmatism. As shown in FIG. 4, both of these screens 155 and 160 are controlled to move in opposite directions. For the purpose of achieving vision correction, the moving screens 120, 155 and 160 of the continuous energy delivery control means are controlled by a computer 170 according to the time-varying movement functions described below.

Referring to FIGS. 5 and 6 for the following description about the time-varying movement function of the moving screens 155 and 160 in order to achieve the astigmatism correction. The profile of the circular laser beam 140 generated by the image rotator and beam homogenizer 130 has an uniform intensity distribution. The edges of the moving screens 155 and 160 are parallel to the astigmatism axis. For the purpose of discussion, the motion of these two screens 155 and 160 are assumed to be along an X-axis. At the beginning the screens 155 and 160 are in contact with each other and no energy from the laser beam 140 is transferred to the cornea 180. As the screen 155 is controlled by the computer 170 moved to the left, the screen 160 is also controlled to move to the right with a movement function X(t). The total energy delivered to the cornea 180 per unit area at point $x_0$ is represented by:

$$E(x_0) = \int_{t_0}^{t_f} I(x_0, y_0) dt \qquad (1)$$

Where $t_0$ is the solution of t in $x_0=X(t)$ and $t_f$ is the finishing time of movement of the screen 155. Since the circular beam 140 has a beam profile of uniform intensity, the above equation can be simplified as:

$$E(x_0) = I(t_f - t_0) \qquad (2)$$

The desired energy per unit area to achieve a cylindrical correction is $$E(x_0) = E(1 - ax^2) \qquad (3)$$

where a is a parameter related to intensity variation wherein if:

$$E(x_0) = 0 \text{ when } X_0 = Xm$$

then $$a = X_m^{-2}.$$

Comparing Equation (3) with Equation (2), a relation between the $x_0$ and $t_0$ can be determined as:

$$x_0 = [t/(at_f)]^{(1/2)} \qquad (4)$$

Equation (4) shows the functional dependence of the position of the edges of the moving screens 155 and 160 with respect to time. The astigmatism correction as represented by Equation (3) By controlling the movement of the moving screens 155 and 160 according to Equation (4) will then achieve.

Referring to FIGS. 7 and 8 for the following description of the movement for the moving screen 120 as function of time for correction of myopia. The screens 115 and 120 are placed in front of the image rotator-beam homogenizer 130 which converts the laser beam into a circular beam 140. The laser energy deposited per unit area at radius r from the center of the beam axis after passing through the image rotator-beam homogenizer 130 can be represented as $$E(r) = \qquad (5)$$

$$\int_0^{t_f} dt \left\{ \Theta(x_0(t) - r) \frac{1}{2\pi} \int_{-\pi/2}^{\pi/2} d\theta [f(r\cos\theta)g(r\sin\theta)] + \right.$$

$$\left. \Theta(r - x_0(t)) \frac{1}{2\pi} \left( \int_\phi^{\pi/2} d\theta + \int_{-\pi/2}^{-\phi} d\theta \right) [f(r\cos\theta)g(r\sin\theta)] \right\}$$

where the time integration is from t=0 to the finishing time at $t=t_f$, while $\Theta$ is a Heairside function defined by:

$$\Theta(y) = 0 \quad \text{if } y \leq 0 \qquad (6)$$
$$\quad = 1 \quad \text{if } y > 0$$

and $$\tan\phi = [(r^2/x_o^2) - 1]^{(1/2)}$$

where $\phi$ is the polar angle corresponding to a point having abscissa $X_0$ and at a distance r from the origin, f(x) is the laser light intensity distribution function in the x direction, and g(y) is the laser light intensity distribution function in the y direction. According to the above equations, the light falls on the region for $r < x_0$ is redistributed into a circular region after passing through image rotator-beam homogenizer 130. Since the screen 115 covers half of the beam, originally the energy deposited is defined by:

$$\Theta(x_0(t) - r) \frac{1}{2\pi} \int_{-\pi/2}^{\pi/2} d\theta [f(r\cos\theta)g(r\sin\theta)] \qquad (7)$$

On the other hand, if $r > x_0$, the energy deposited between r and r+dr is:

$$\Theta(r - x_0(t)) \frac{1}{2\pi} \left( \int_\phi^{\pi/2} d\theta + \int_{-\pi/2}^{-\phi} d\theta \right) [f(r\cos\theta)g(r\sin\theta)] \qquad (8)$$

The energy is to be spread out into circular ring with radii of r and r+dr.

With the laser light intensity distribution f(x) and g(y) in the direction of x and y respectively, and the desired energy distribution E(r) the equation for $x_0=x_0(t)$ can be solved numerically using computer. For the myopia correction, E(r) is of the form:

$$E(r) = E(0)(1 - ar^2) \quad a = r_0^{-2} \qquad (9)$$

A program is executed by the microprocessor controller 170 in carrying out a numerical analysis of Equations (7), (8), and (9) for the determination of movement function $x_0(t)$. The microprocessor controller 170 then controls the movement of the moving screens 155 and 160 according to the numerical solution obtained for $x_0(t)$ to deposit the laser energy delivered by the circular laser beam 140 to the cornea according to Equation (9) for myopia correction.

For the correction of hyperopia, the moving screen 155 is controlled to move to the left from an initial position of being overlapped with the moving screen 160 thus blocking the entire circular laser beam 140 at the beginning of operation, i.e., t=0. As the moving screen 155 is controlled by the microprocessor controller 170 to move to the left thus uncovering the right hand side of the opening. The movement of the right edge of the moving screen 155 as a function of time, i.e., $x_0(t)$, can be controlled to deposit a predetermined amount of energy distributed over the surface area the cornea to achieve the hyperopia correction. The energy deposited per area after passing through the image rotator-beam homogenizer is represented by:

$$E(r) = \int_0^{t_f} dt \left\{ \Theta(r - x_0(t)) \frac{1}{2\pi} \int_{-\phi}^{\phi} [f(r\cos\theta)g(r\sin\theta)d\theta] \right\} \quad (10)$$

For the purpose of hyperopia correction, the desired energy distribution is:

$$E(r) = br^2 \quad (11)$$

In addition to controlling the movements of the moving screens 120, 155, and 160 for performing the vision correction as described above, the microprocessor controller 170 also controls the power of the laser source 105. Assuming the laser beam intensity of the circular laser beam 140 is uniform, and assuming that the motion x(t) of the moving screen 155 or 160 is represented by:

$$(t/t_f) = 1 - [x(t)^2/x_m^2] \quad (12)$$

Where $x_m$ is the maximum value of x(t) and $t_f$ is total duration of time that energy is delivered by the laser beam to deposit on the cornea. The intensity I(r) of the circular laser beam 140 right after the image-rotator homogenizer 130 can be represented as:

$$I(r) = I_0[r/(2x_m)]^2 \quad (13)$$

where r is the distance from the optical axis of the circular laser beam 140, and $I_0$ is the beam intensity along the optical axis. The central beams intensity $I_0$ depends on the design of the excimer laser source 105.

The amount of cornea tissue removed as the result of vision correction operation depending on the power of correction to be achieved. The depth of the corneal tissue to be removed is related to the change in curvature. The functional dependence can be expressed as:

$$D = r^2[1/(2R_2) - 1/(2R_1)] \quad (14)$$

where D is the depth of corneal tissue removed, r is the distance from the optical axis of the eye, $R_1$ is the radius of curvature of the cornea before the correction, and $R_2$ is the radius of curvature of the cornea after the correction, and the power of vision correction P in the unit of diopter which can be represented by:

$$P = (n-1)[1/(2R_2) - 1/(2R_1)] \quad (15)$$

From Equations (14) and (15), the relationship between the depth for corneal tissue removal as a function of the vision correction power P can be derived as:

$$D = [P/(n-1)]r^2 \quad (16)$$

where n is the index of refraction of the cornea. The maximum depth of cornea ablation in the unit of microns and the diameter of the circle of laser ablation in the unit of millimeter (mm) in order to achieve the power of vision correction in the unit of diopter is summarized in Table 1 assuming a refractive index n to be 1.376. This table is applicable to both myopia and hyperopia corrections. For myopia correction, the maximum depth occurs at the center of the ablation circle, while for the hyperopia correction, the maximum, depth occurs at the edge of the ablation circle.

The moving screens 115, 120, 155, and 160 employed in the continuous energy-delivery control system as shown above can be replaced by screens with variable transparency. Instead of the moving screens, the continuous energy-delivery control system can also employ rotating diaphragms which may be opaque or may be diaphragms with variable transparency. There may be many different varieties of optical designs to achieve the identical corrective results. The basic principle is to control the energy delivery system in a manner such that smooth and continuous delivery of laser energy is carried out to achieve high precision vision correction with smooth ablation on the cornea without requiring the change of aperture masks.

Figure 9:
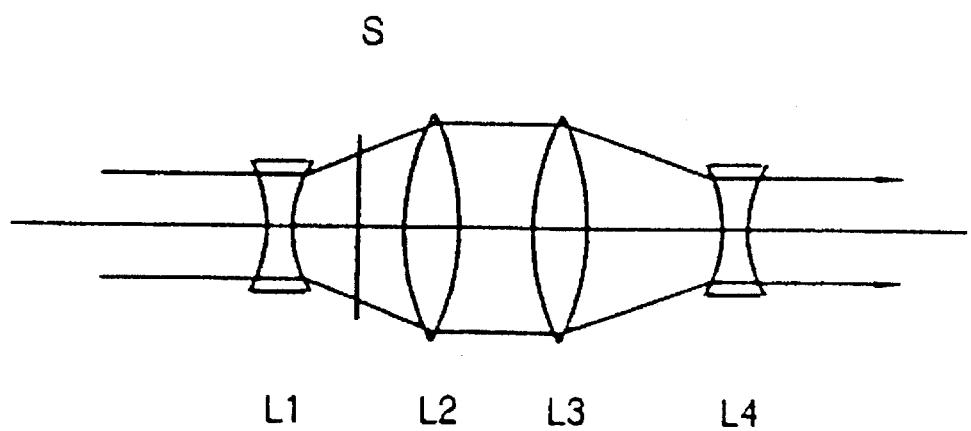
FIG. 9 shows a continuous energy-delivery control means which utilizes a lens system with a moving screen with variable transparency.

FIG. 9 shows the another preferred embodiment of the continuous energy-delivery control system 200 of the present invention. The continuous energy-delivery control system 200 employs a combination of a lens systems which includes four lenses L1, L2, L3, and L4 arranged on a common optical axis 210 and a moving screen 220 moving along the optical axis 210 between lenses L1 and L2 wherein L1 and L4 are concave lenses and L2 and L3 are convex lenses. The moving screen 220 is a screen with variable transparency. It is advantageous to make the incoming laser beam 230 and the outgoing laser beam 240 parallel. It is achieved by arranging the focal point of the convex lens L2 to be located at the virtual focal point of the lens L1. Similarly, the focal point of the convex lens L3 is arranged to be located at the virtual focal point of the concave lens L4. The incoming laser beam 230 first passes through the concave lens L1 and the moving screen 220 to reach the convex lenses L2, L3 and the concave lens L4 to deliver the laser energy to the cornea. The moving screen has variable transparency serves as a variable density absorbing filter which is controlled by a microprocessor to move according to a predetermined time-varying movement function to achieve a specific corrective result.

Figure 10:
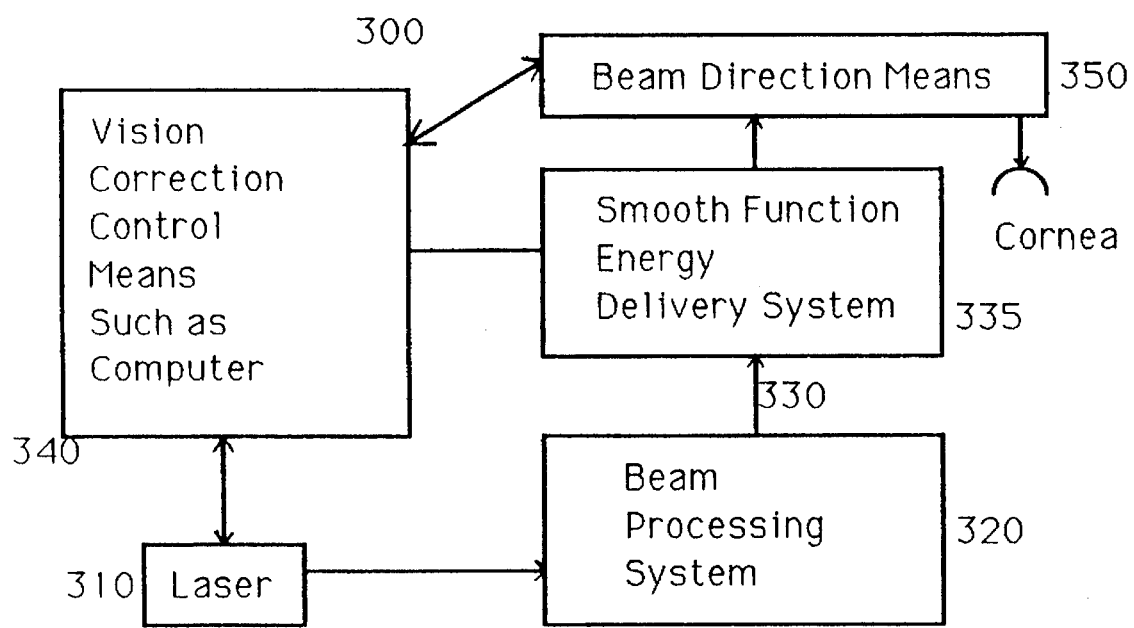
FIG. 10 is a system diagram showing the energy delivery system of the present invention for performing a photorefractive keratectomy.

The present invention thus provides an energy delivery system 300 as that shown in FIG. 10 for laser photorefractive keratectomy. The energy delivery system 300 receives a processed laser beam 330 from a laser beam source 310 after the beam is processed by a beam processing system 320. The processed laser beam 330 is applied to a continuous energy-delivery control means 340 which controls the delivery of the laser energy to the surface of a cornea 360 via a beam direction means 350 according to the vision correction requirements. Depending on different vision correction requirements, the continuous energy-delivery control means 335 and the laser source 310 is controlled by a vision correction control means 340 which may be a computer to adjust the laser beam intensity and the moving screens, the rotating diaphragms or the lens system included in the continuous energy-delivery control means to achieve a predetermined vision correction to be performed on the surface of the cornea 360. Because of the use of the continuous energy-delivery control means, the operation under the control of the computer, i.e., the vision correction control means 340, the PK operation can be performed in a continuous manner as a single operation. The need for interrupting the operation for changing discrete aperture masks and realigning the optical system is therefore eliminated with the present invention.

Specifically, an optical system for performing a laser photorefractive keratectomy operation on a cornea for vision correction is disclosed in the present invention. This optical system 300 comprises a laser source 310 emitting a laser beam therefrom. The optical system also includes a beam processing means 320 for receiving and processing the laser beam for generating a processed laser beam 330 suitable for performing the keratectomy operation. The optical system further includes an energy delivery means which includes at a continuous energy-delivery control means 335 for optically controlling the energy delivered to different areas of the cornea 360 by the processed laser beam for vision correction. In a preferred embodiment, the energy delivery means including the continuous energy-delivery control means 335 are being controlled by a microprocessor 340. In yet another preferred embodiment, the continuous energy-delivery control means 335 includes at least one optical shutter, e.g., shutter including screens 115, 120, 155, or 160, which may be controlled to move continuously in performing the photorefractive keratectomy operation.

The present invention thus provides a new technique in the design of the energy delivery system for photorefractive keratectomy to overcome the difficulties encountered in the prior art. Specifically, the present invention provides an energy delivery system for photorefractive keratectomy to produce smooth laser ablation on the cornea for vision correction by utilizing continuous energy-delivery control means under computer control to deliver precise laser energy to the cornea. The efficiency of the photorefractive keratectomy operation is improved without requiring the change of aperture masks and realignment of the optical system. The surgery time can also be shortened. Furthermore, since the present invention provides an energy delivery system for photorefractive keratectomy with the continuous energy-delivery control means totally under the control of computer without requiring frequency human intervention, higher precision of vision correction can be achieved while human errors in operation can be reduced.

Although the present invention has been described in terms of the presently preferred embodiment, it is to be understood that such disclosure is not to be interpreted as limiting. Various alternations and modifications will no doubt become apparent to those skilled in the art after reading the above disclosure. Accordingly, it is intended that the appended claims be interpreted as covering all alternations and modifications as fall within the true spirit and scope of the invention.

TABLE 1

Maximum depth of laser cornea ablation in microns as a function of the power of corrective lens in diopter and diameter of the circle of laser cornea ablation in mm.

| Power of corrective lens in diopter | Diameter of the circle of laser cornea ablation in mm | | | | | | | | |
|---|---|---|---|---|---|---|---|---|---|
| | d = 4 | d = 4.5 | d = 5 | d = 5.5 | d = 6 | d = 6.5 | d = 7 | d = 7.5 | d = 8 |
| 0.25 | 3 | 3 | 4 | 5 | 6 | 7 | 8 | 9 | 11 |
| 0.50 | 5 | 7 | 8 | 10 | 12 | 14 | 16 | 19 | 21 |
| 0.75 | 8 | 10 | 12 | 15 | 18 | 21 | 24 | 28 | 32 |
| 1.00 | 11 | 13 | 17 | 20 | 24 | 28 | 33 | 37 | 43 |
| 1.25 | 13 | 17 | 21 | 25 | 30 | 35 | 41 | 47 | 53 |
| 1.50 | 16 | 20 | 25 | 30 | 36 | 42 | 49 | 56 | 64 |
| 1.75 | 19 | 24 | 29 | 35 | 42 | 49 | 57 | 65 | 74 |
| 2.00 | 21 | 27 | 33 | 40 | 48 | 56 | 65 | 75 | 85 |
| 2.25 | 24 | 30 | 37 | 45 | 54 | 63 | 73 | 84 | 96 |
| 2.50 | 27 | 34 | 42 | 50 | 60 | 70 | 81 | 94 | 106 |
| 2.75 | 29 | 37 | 46 | 55 | 66 | 77 | 90 | 103 | 117 |
| 3.00 | 32 | 40 | 50 | 60 | 72 | 84 | 98 | 112 | 128 |
| 3.25 | 35 | 44 | 54 | 65 | 78 | 91 | 106 | 122 | 138 |
| 3.50 | 37 | 47 | 58 | 70 | 84 | 98 | 114 | 131 | 149 |
| 3.75 | 40 | 50 | 62 | 75 | 90 | 105 | 122 | 140 | 160 |
| 4.00 | 43 | 54 | 66 | 80 | 96 | 112 | 130 | 150 | 170 |
| 4.25 | 45 | 57 | 71 | 85 | 102 | 119 | 138 | 159 | 181 |
| 4.50 | 48 | 61 | 75 | 91 | 108 | 126 | 147 | 168 | 191 |
| 4.75 | 51 | 64 | 79 | 96 | 114 | 133 | 155 | 178 | 202 |
| 5.00 | 53 | 67 | 83 | 101 | 120 | 140 | 163 | 187 | 213 |
| 5.25 | 56 | 71 | 87 | 106 | 126 | 147 | 171 | 196 | 223 |
| 5.50 | 59 | 74 | 91 | 111 | 132 | 155 | 179 | 206 | 234 |
| 5.75 | 61 | 77 | 96 | 116 | 138 | 162 | 187 | 215 | 245 |
| 6.00 | 64 | 81 | 100 | 121 | 144 | 169 | 195 | 224 | 255 |
| 6.25 | 66 | 84 | 104 | 126 | 150 | 176 | 204 | 234 | 266 |
| 6.50 | 69 | 88 | 108 | 131 | 156 | 183 | 212 | 243 | 277 |
| 6.75 | 72 | 91 | 112 | 136 | 162 | 190 | 220 | 252 | 287 |
| 7.00 | 74 | 94 | 116 | 141 | 168 | 197 | 228 | 262 | 298 |
| 7.25 | 77 | 98 | 121 | 146 | 174 | 204 | 236 | 271 | 309 |
| 7.50 | 80 | 101 | 125 | 151 | 180 | 211 | 244 | 281 | 319 |
| 7.75 | 82 | 104 | 129 | 156 | 186 | 218 | 252 | 290 | 330 |
| 8.00 | 85 | 108 | 133 | 161 | 191 | 225 | 261 | 299 | 340 |
| 8.25 | 88 | 111 | 137 | 166 | 197 | 232 | 269 | 309 | 351 |
| 8.50 | 90 | 114 | 141 | 171 | 203 | 239 | 277 | 318 | 362 |
| 8.75 | 93 | 118 | 145 | 176 | 209 | 246 | 285 | 327 | 372 |
| 9.00 | 96 | 121 | 150 | 181 | 215 | 253 | 293 | 337 | 383 |
| 9.25 | 98 | 125 | 154 | 186 | 221 | 260 | 301 | 346 | 394 |
| 9.50 | 101 | 128 | 158 | 191 | 227 | 267 | 310 | 355 | 404 |
| 9.75 | 104 | 131 | 162 | 196 | 233 | 274 | 318 | 365 | 415 |
| 10.00 | 106 | 135 | 166 | 201 | 239 | 281 | 326 | 374 | 426 |

We claim:

1. An optical system for performing a laser photorefractive keratectomy operation on a cornea for vision correction comprising:

a laser source emitting a laser beam therefrom;

a beam processing means for receiving and processing said laser beam for generating a processed laser beam suitable for performing said keratectomy operation wherein said beam processing means including an image rotator and a beam homogenizer; and an energy delivery means including a continuous energy-delivery control means cooperating with said beam processing means for optically controlling the energy delivered by said processed laser beam to different areas of said cornea for vision correction wherein said continuous energy-delivery control system includes moving slits disposed in front of said image rotator and said beam homogenizer for corrections of myopia and hyperopia.

2. The optical system as set forth in claim 1 wherein:

said energy delivery means including said continuous energy-delivery control means is being controlled by a microprocessor.

3. The optical system as set forth in claim 2 wherein:

said moving slits disposed in front of said image rotator and said beam homogenizer further includes at least one optical shutter which may be controlled to move continuously in performing said photorefractive keratectomy operation.

4. The optical system as set forth in claim 3 wherein:

said continuous energy-delivery control means further includes a movable screen of variable transparency controlled by said microprocessor to move for controlling the energy delivered to different areas of said cornea.

5. The optical system as set forth in claim 3 wherein:

said continuous energy-delivery control means includes an astigmatism correction energy-delivery control means which includes two movable opaque screens controlled by said microprocessor for controlling the energy delivered to different areas of said cornea for astigmatism correction.

6. An optical system for performing a laser photorefractive keratectomy operation on a cornea for vision correction comprising:

a laser source emitting a laser beam therefrom;

a beam processing means including an image rotator and a beam homogenizer for receiving and processing said laser beam for generating a processed laser beam suitable for performing said keratectomy operation;

an energy delivery means including a continuous energy-delivery control means cooperating with said beam processing means for optically controlling the energy delivered by said processed laser beam to different areas of said cornea for vision correction wherein said continuous energy-delivery control system includes moving slits disposed in front of said image rotator and said beam homogenizer for corrections of myopia and hyperopia;

said continuous energy-delivery control means further includes a movable screen of variable transparency; and said continuous energy-delivery control means includes said moving slits and said moveable screen of variable transparency are controlled by said microprocessor for vision correction.

7. A method for performing a laser photorefractive keratectomy operation on a cornea for vision correction comprising the step of:

(a) emitting a laser beam from a laser source;

(b) receiving and processing said laser beam by employing a beam processing means for generating a processed laser beam suitable for performing said keratectomy operation; and (c) employing an energy delivery means including a continuous energy-delivery control means, having two moving slits disposed in front of said beam processing means, cooperating with said beam processing means for optically controlling the energy delivered by said processed laser beam to different areas of said cornea for myopia/hyperopia correction.

8. The method for vision correction as set forth in claim 7 further comprising a step of:

(d) controlling said energy delivery means including said continuous energy-delivery control means by employing a microprocessor.

9. The method for vision correction as set forth in claim 8 wherein:

said step (c) in optically controlling the energy delivered by said processed laser beam further including a step of employing at least one optical shutter as one of said moving slits controllable to move continuously in performing said myopia/hyperopia correction.

10. The method for vision correction as set forth in claim 9 wherein:

said step (c) in optically controlling the energy delivered by said processed laser beam further includes a step of employing a moveable screen of variable transparency controlled by said microprocessor for controlling the energy delivered to different areas of said cornea for vision correction.

11. The method for vision correction as set forth in claim 9 wherein:

said step (c) in optically controlling the energy delivered by said processed laser beam further including a step of employing a astigmatism correction energy-delivery control means including two movable opaque screens controlled by said microprocessor for controlling the energy delivered to different areas of said cornea for astigmatism correction.

* * * * *